US010928465B2

(12) United States Patent
Govari

(10) Patent No.: US 10,928,465 B2
(45) Date of Patent: Feb. 23, 2021

(54) MAGNETIC TRANSMITTERS FOR A MAGNETIC TRACKING SYSTEM

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 61 days.

(21) Appl. No.: 16/178,701

(22) Filed: Nov. 2, 2018

(65) Prior Publication Data
US 2020/0142011 A1    May 7, 2020

(51) Int. Cl.
*G01R 33/28* (2006.01)
*G01R 33/483* (2006.01)
*G01R 33/3815* (2006.01)
*G01R 33/34* (2006.01)

(52) U.S. Cl.
CPC .......... *G01R 33/287* (2013.01); *G01R 33/34* (2013.01); *G01R 33/3815* (2013.01); *G01R 33/483* (2013.01)

(58) Field of Classification Search
None
See application file for complete search history.

(56) References Cited

U.S. PATENT DOCUMENTS

| 5,045,792 | A | 9/1991 | Mehdizadeh |
| 5,394,087 | A | 2/1995 | Molyneaux |
| 5,833,608 | A | 11/1998 | Acker |
| 5,898,306 | A | 4/1999 | Liu et al. |
| 6,332,089 | B1 | 12/2001 | Acker et al. |
| 2014/0018664 | A1 | 1/2014 | Weiss et al. |

FOREIGN PATENT DOCUMENTS

| EP | 3646810 A1 * | 5/2020 | .......... G01R 33/287 |
| KR | 20170034393 A | 3/2017 | |

OTHER PUBLICATIONS

Coutts et al., Integrated and interactive position tracking and imaging of interventional tools and internal devices using small fiducial receiver coils, Magnetic Resonance in Medicine, vol. 40, Issue 6, Dec. 1998, pp. 908-913.
Extended European Search Report for corresponding European patent application no. 19206705.6, dated Feb. 13, 2020.

* cited by examiner

*Primary Examiner* — Jermele M Hollington
(74) *Attorney, Agent, or Firm* — Notaro, Michalos & Zaccaria P.C.

(57) ABSTRACT

Apparatus, having a frame encompassing a volume. The apparatus includes three pairs of separated planar conductive coils, the separated coils of each pair having a common axis of symmetry, the three pairs being attached to the frame so that the common axes of symmetry are mutually orthogonal, and so that the coils surround the volume. An alternating current power supply is coupled to drive the separated coils of each pair in anti-phase so as to generate a magnetic field having a preset spatial variance over the volume. The apparatus also includes a probe that is configured to enter the volume and that has a sensor coupled to generate a signal responsive to a temporal rate of change of the magnetic field and to the preset spatial variance thereof. A processor is configured to receive the signal and in response formulates a position of the probe within the volume.

28 Claims, 7 Drawing Sheets

MAGNETIC TRANSMITTERS FOR A MAGNETIC TRACKING SYSTEM

FIELD OF THE INVENTION

This invention relates generally to magnetic tracking systems, and specifically to design of the transmitters used in the systems.

BACKGROUND OF THE INVENTION

Magnetic tracking systems, wherein magnetic transmitters radiate into a space, may be used to track a probe in the space if the probe has a sensor that is able to measure the radiated field. The tracking assumes that the radiated field from the transmitters has been calibrated, so that a measurement of the radiated field value can be used to derive a position of the probe.

In a number of cases the calibration is compromised because of metallic elements in, or close to, the radiated space. For example, the metal, even though it is non-magnetic, of a magnetic resonance imaging (MRI) scanner may affect the calibration of the tracking system.

U.S. Pat. No. 5,833,608, to Acker, describes a magnetic position and orientation determining system. The system uses magnetic fields, including uniform fields from Helmholtz coils positioned on opposite sides of a sensing volume and gradient fields generated by the same coils.

U.S. Patent Application 2014/0018664, to Weiss et al., describes a magnetic resonance imaging system having an open magnet. In the open magnet two superconducting coils are mounted on top of each other and they produce a magnetic field similar that of a Helmholtz coil.

An article entitled "Integrated and interactive position tracking and imaging of interventional tools and internal devices using small fiducial receiver coils" by Coutts et al. published in Volume 40, Issue 6 (December 1998) of Magnetic Resonance in Medicine, describes tracking the position of a rigid device within an MR scanner. The position tracking is performed by means of two or three small MR receiver coils attached to individual receiver channels.

U.S. Pat. No. 5,394,087, to Molyneaux, describes a multiple quadrature surface coil system for simultaneous imaging in magnetic resonance systems.

SUMMARY OF THE DISCLOSURE

An embodiment of the present invention provides apparatus, including:

a frame encompassing a volume;

three pairs of separated planar conductive coils, the separated coils of each pair having a common axis of symmetry, the three pairs being attached to the frame so that the common axes of symmetry are mutually orthogonal, and so that the coils surround the volume;

an alternating current power supply coupled to drive the separated coils of each pair in anti-phase so as to generate a magnetic field having a preset spatial variance over the volume;

a probe configured to enter the volume and having a sensor coupled to generate a signal responsive to a temporal rate of change of the magnetic field and to the preset spatial variance thereof; and a processor, configured to receive the signal, and in response to formulate a position of the probe within the volume.

In a disclosed embodiment the separated coils of each pair have a common size and shape. The common shape of at least one of the pairs may be circular. Alternatively or additionally, the common shape of at least one of the pairs is polygonal.

In a further disclosed embodiment the frame and attached pairs have an overall size permitting insertion of the frame and attached pairs into a bore of a magnetic resonance imaging scanner.

In a yet further disclosed embodiment at least one of the pairs of coils is wound in opposite directions, and the alternating current power supply provides power to the coils in the one of the pairs with in-phase current.

In an alternative embodiment at least one of the pairs of coils is wound in a common direction, and the alternating current power supply provides power to the coils in the one of the pairs with out-of-phase current.

In a further alternative embodiment for a given pair of coils the preset spatial variance of the magnetic field includes a region wherein the magnetic field is linearly varying along the common axis of symmetry of the given pair. Each of the coils of the given pair may have a radius R, and a separation between the coils of the given pair may be within a range between R and 2.8R.

In a yet further alternative embodiment for a given pair of coils the preset spatial variance of the magnetic field includes no region wherein the magnetic field is linearly varying along the common axis of symmetry of the given pair. Each of the coils of the given pair may have a radius R, and a separation between the coils of the given pair may be outside a range between R and 2.8R.

The alternating current power supply may be coupled to drive each of the three pairs of coils sinusoidally in anti-phase at different respective frequencies, so as to generate the temporal rate of change of the magnetic field.

Typically, the three pairs of coils include three respective midpoints, and the three pairs are attached to the frame so that the three midpoints are located at a single point.

The processor may be configured to formulate an orientation of the probe within the volume in response to the received signal.

There is further provided, according to an embodiment of the present invention, a method, including:

encompassing a volume with a frame;

attaching to the frame three pairs of separated planar conductive coils, the separated coils of each pair having a common axis of symmetry, so that the common axes of symmetry are mutually orthogonal, and so that the coils surround the volume;

coupling an alternating current power supply to drive the separated coils of each pair in anti-phase so as to generate a magnetic field having a preset spatial variance over the volume;

inserting a probe into the volume, the probe having a sensor coupled to generate a signal responsive to a temporal rate of change of the magnetic field and to the preset spatial variance thereof; and receiving the signal, and in response formulating a position of the probe within the volume.

The present disclosure will be more fully understood from the following detailed description of the embodiments thereof, taken together with the drawings, in which:

DETAILED DESCRIPTION OF EMBODIMENTS

Overview

Figure 1:
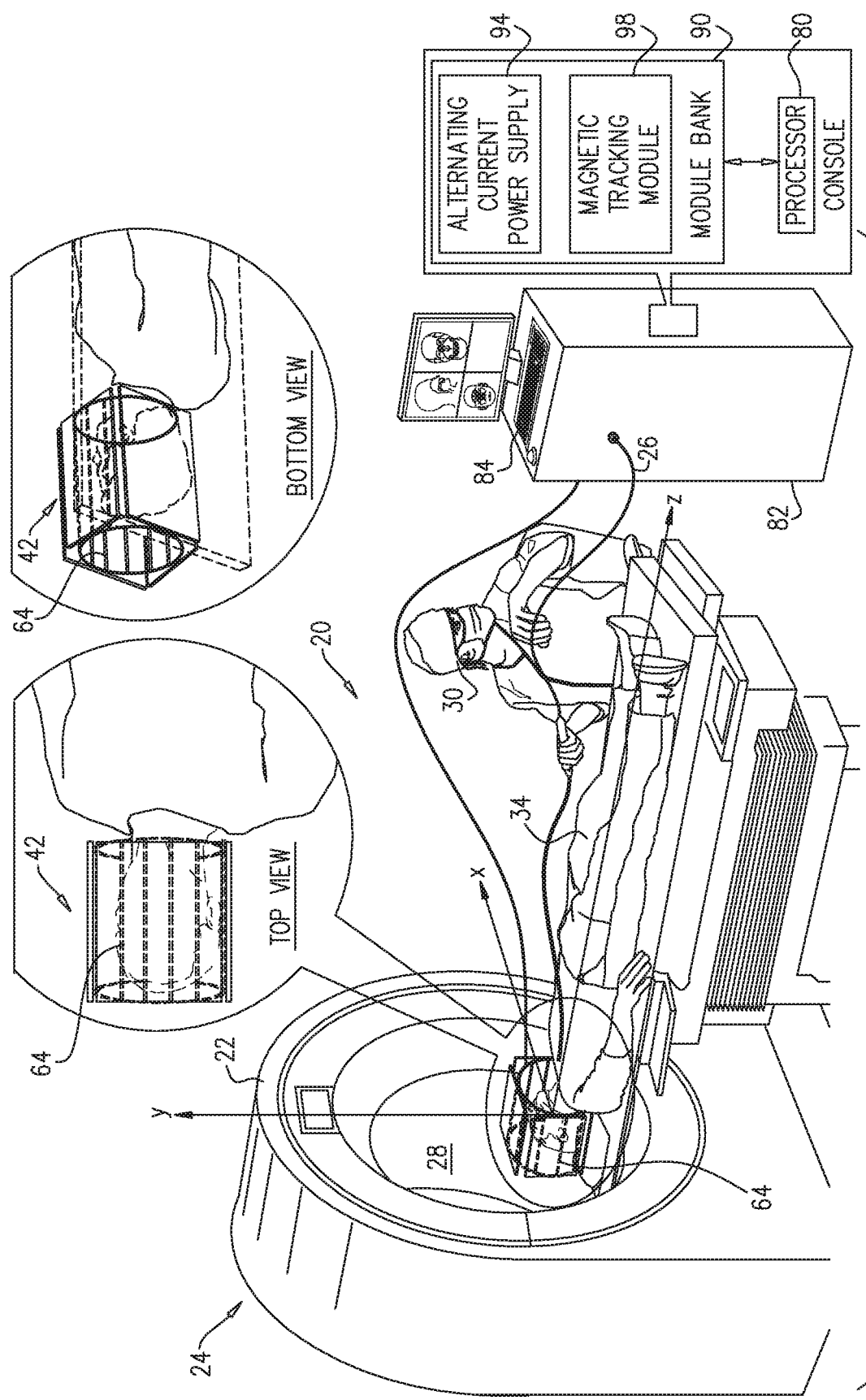
FIGS. 1 and 2 are schematic illustrations of a tracking apparatus, according to an embodiment of the present invention.

While present day magnetic tracking systems may be operated in a region having non-magnetic metals, the presence of the non-magnetic metals imposes limitations on the tracking system. For example, in a magnetic resonance imaging (MRI) scanner, the metal of the MRI scanner leads to distortions in the magnetic field generated by the transmitters of the magnetic tracking system. The field from the transmitters is typically calibrated prior to the transmitters being introduced into the MRI system, but the introduction leads to errors in the calibration. The errors may be large because the tracking field transmitters are typically relatively far from a tracking volume wherein objects are to be tracked.

Embodiments of the present invention overcome these problems by configuring the tracking field transmitters to comprise sets of coils that enclose the tracking volume. The sets of coils are mounted on a frame, and the coils and frame combination may be dimensioned so as to be insertable into the bore of the MRI scanner. The tracking volume is thus relatively far from MRI metal.

An embodiment of the invention comprises a frame encompassing a volume, and there are three pairs of separated planar conductive coils attached to the frame. Each of the pairs has a respective common axis of symmetry, and the three pairs are attached to the frame so that the three axes of symmetry are mutually orthogonal.

An alternating current power supply is coupled to drive the separated coils of each pair in anti-phase so as to transmit a magnetic field having a preset spatial variance and temporal rate of change into the volume.

A probe, having a sensor coupled to generate a signal responsive to the preset spatial variance and to the temporal rate of change of the magnetic field, may be inserted into the volume, and a processor may be configured to receive the signal. The processor may use the signal to formulate a position and an orientation of the probe in the volume.

DETAILED DESCRIPTION

In the following description, like elements in the drawings are identified by like numerals, and like elements are differentiated as necessary by appending a letter to the identifying numeral.

Figure 2:
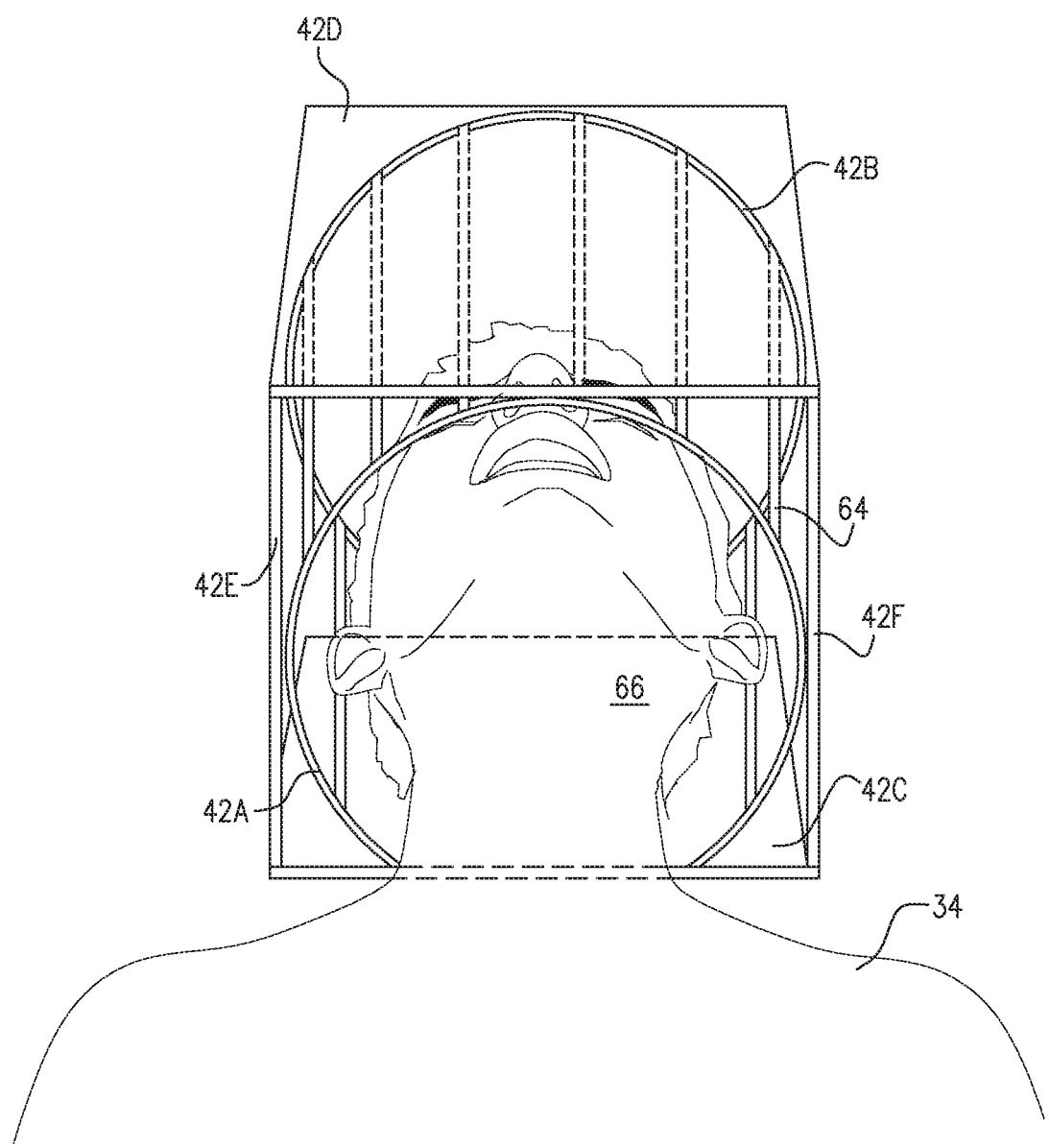

FIGS. 1 and 2 are schematic illustrations of a tracking apparatus 20, according to an embodiment of the present invention. Apparatus 20 is typically configured to be used in a magnetic resonance imaging (MRI) environment, and in the description hereinbelow, the apparatus is assumed to be used in conjunction with an MRI scanner 22. Scanner 22 is assumed to define an orthogonal set of xyz axes, as illustrated in FIG. 1, wherein an axis of symmetry of a bore 28 of the scanner is assumed to define a horizontal z-axis for the scanner, there is a vertical y-axis, and an x-axis orthogonal to both the z- and the y-axes. The origin of the orthogonal axes is assumed to correspond to the center of bore 28. However, those having skill in the art will appreciate that apparatus 20 is not confined to being used with an MRI scanner, so that the scope of the present invention comprises use in a non-MRI environment.

In the description herein, apparatus 20 is used to track the position and orientation of a probe 24 at the distal end of a catheter 26, wherein the probe has been inserted into an organ of a patient 34 undergoing a medical procedure, and the patient has been placed within bore 28. The procedure is performed by a medical professional 30. By way of example, the organ is considered to comprise the nasal sinuses of patient 34, and the procedure is assumed to comprise radiofrequency (RF) ablation of a portion of the sinuses. However, those having skill in the art will be able to alter the description, mutatis mutandis, for other procedures and for other organs of patient 34, such as electrophysiology mapping of the heart.

As is described in more detail below, in order to track probe 24 the probe is placed in a magnetic field having a known spatial and temporal variation, and a magnetic sensor disposed within the probe measures the magnetic field traversing the probe. The measured magnetic field is used to determine the location, i.e., both the position and the orientation, of the probe.

In order to perform the procedure referred to above, a protective cage 64 is placed over the head of patient 34, and the patient's head, with the cage, is inserted into bore 28 of scanner 22. FIG. 2 is a schematic diagram of protective cage 64, showing an alternative view of the cage from the views shown in FIG. 1. Typically, prior to being placed over the patients' head, six conductive coils 42A, 42B, 42C, 42D, 42E, and 42F are attached to cage 64, and coils 42A, 42B, 42C, 42D, 42E, and 42F are also referred to herein as coils 42. Cage 64 acts as a frame to which coils 42 are attached, and is also herein termed frame 64. Frame 64 is assumed to encompass a volume 66, so that the coils attached to the frame bound the volume.

Coils 42 are formed as three pairs (42A, 42B), (42C, 42D), and (42E, 42F) of planar coils, and the planar coils may be circular, or any convenient, typically polygonal, shape, so long as the two coils of a pair have substantially the same size and shape. However, there is no necessity for the coils of different pairs to have the same shape, and in some embodiments the shape of the coils is selected to conform to the shape of frame 64. By way of example FIG. 2 illustrates one pair (42A, 42B) of coils with circular coils, and the other two pairs, (42C, 42D) and (42E, 42F), with rectangular coils.

Figure 3:
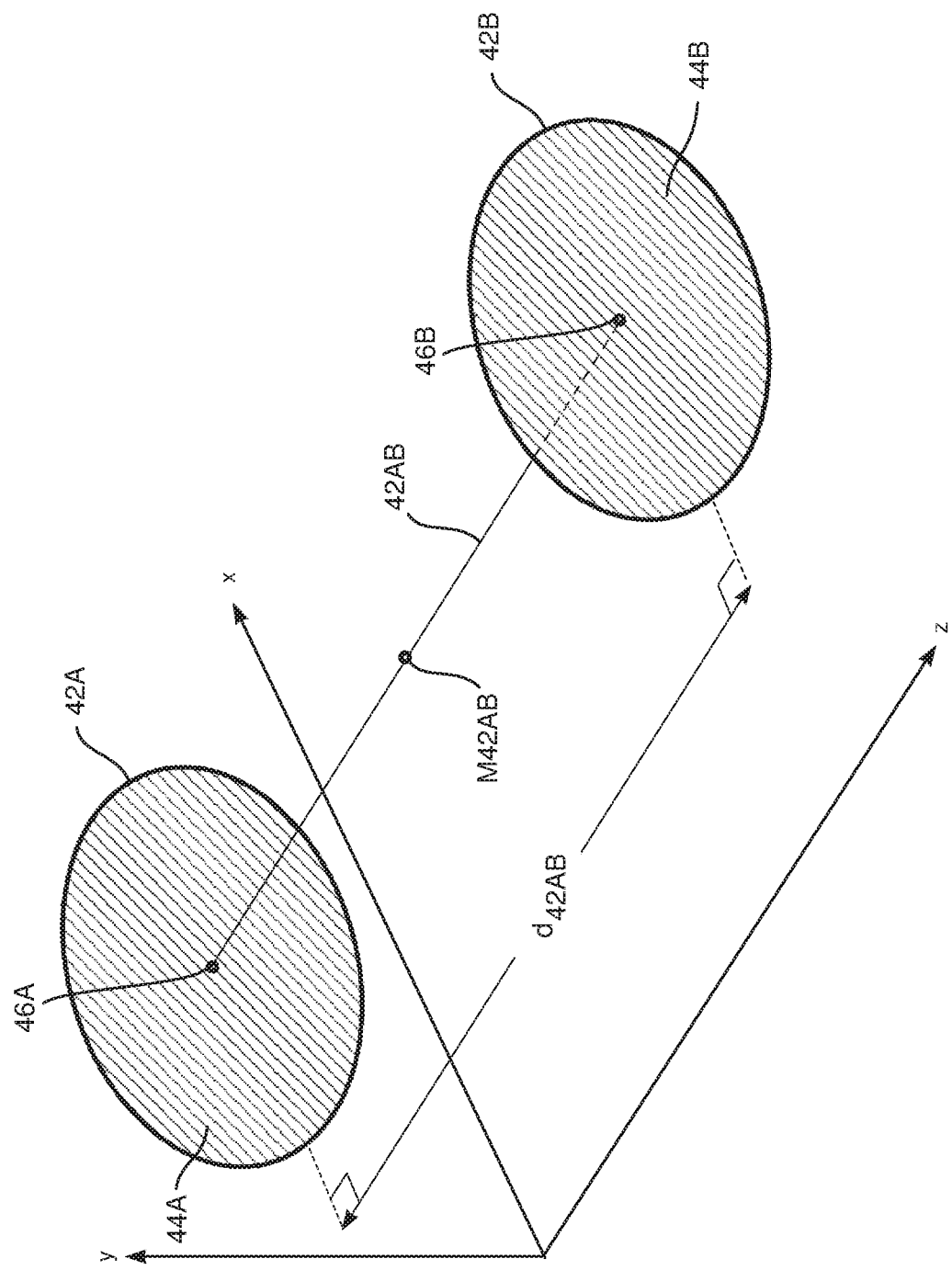
FIG. 3 is a schematic diagram illustrating elements of a pair of coils, according to an embodiment of the present invention.

FIG. 3 is a schematic diagram illustrating elements of pair (42A, 42B) of coils, according to an embodiment of the present invention. For clarity, in FIG. 3 the xyz axes of FIG. 1 have been translated so that coil 42A is on the z=0 plane, and so that a center of the coil is not on the z axis. Coils 42A, 42B define respective planes 44A, 44B, and each coil of the pair has a respective center 46A, 46B. While in the example described in FIG. 3 the coils are circular and so have a center at the center of the circular coil, in general for non-circular coils the center of a coil is assumed to comprise the center of mass of the coil.

Coils 42A, 42B are separated from each other, and are positioned so that planes 44A, 44B are parallel to each other, and so that a line segment 42AB joining the centers of the coils is orthogonal to the planes. Line segment 42AB is assumed to have a length $d_{42AB}$, and is assumed to define a pair axis, which for coils 42A, 42B is also a symmetry axis of the coils. In addition, line segment 42AB has a midpoint M42AB.

Except for being oriented differently, coil pairs (42C, 42D) and (42E, 42F) have generally the same configuration as pair (42A, 42B). I.e., the coils of any given pair are separated from each other, and are positioned so that the planes of the coils are parallel, and so that the planes are orthogonal to a line segment joining the coil centers. In embodiments of the invention the three pairs of coils are attached to frame 64 so that axes of the three pairs of coils are mutually orthogonal, and so that the midpoints of each line segment are at a common point.

Returning to FIG. 1, the common point of the midpoint of the three pairs of coils of apparatus 20 is assumed to be at the origin of the xyz axes. Apparatus 20 is controlled by a system processor 80, which is located in an operating console 82 of the apparatus. Console 82 comprises controls 84 which are used by professional 30 to communicate with the processor. The software for processor 80 may be downloaded to the processor in electronic form, over a network, for example. Alternatively or additionally, the software may be provided on non-transitory tangible media, such as optical, magnetic, or electronic storage media.

In the description herein processor 80 is assumed to be formed from any suitable integrated circuits, including, but not limited to, an ASIC (application specific integrated circuit), an FPGA (field-programmable gate array), an MCU (microcontroller unit), and a CPU (central processing unit).

In order to operate apparatus 20, processor 80 communicates with a module bank 90, which has a number of modules used by the processor to operate the apparatus. Thus, bank 90 comprises an alternating current power supply 94 and a magnetic tracking module 98, the functions of which are described below. Bank 90 typically comprises other modules, such as a force module for measuring the force on probe 24. For simplicity, such other modules are not illustrated in FIG. 1. The modules may comprise hardware as well as software elements.

Figure 4:
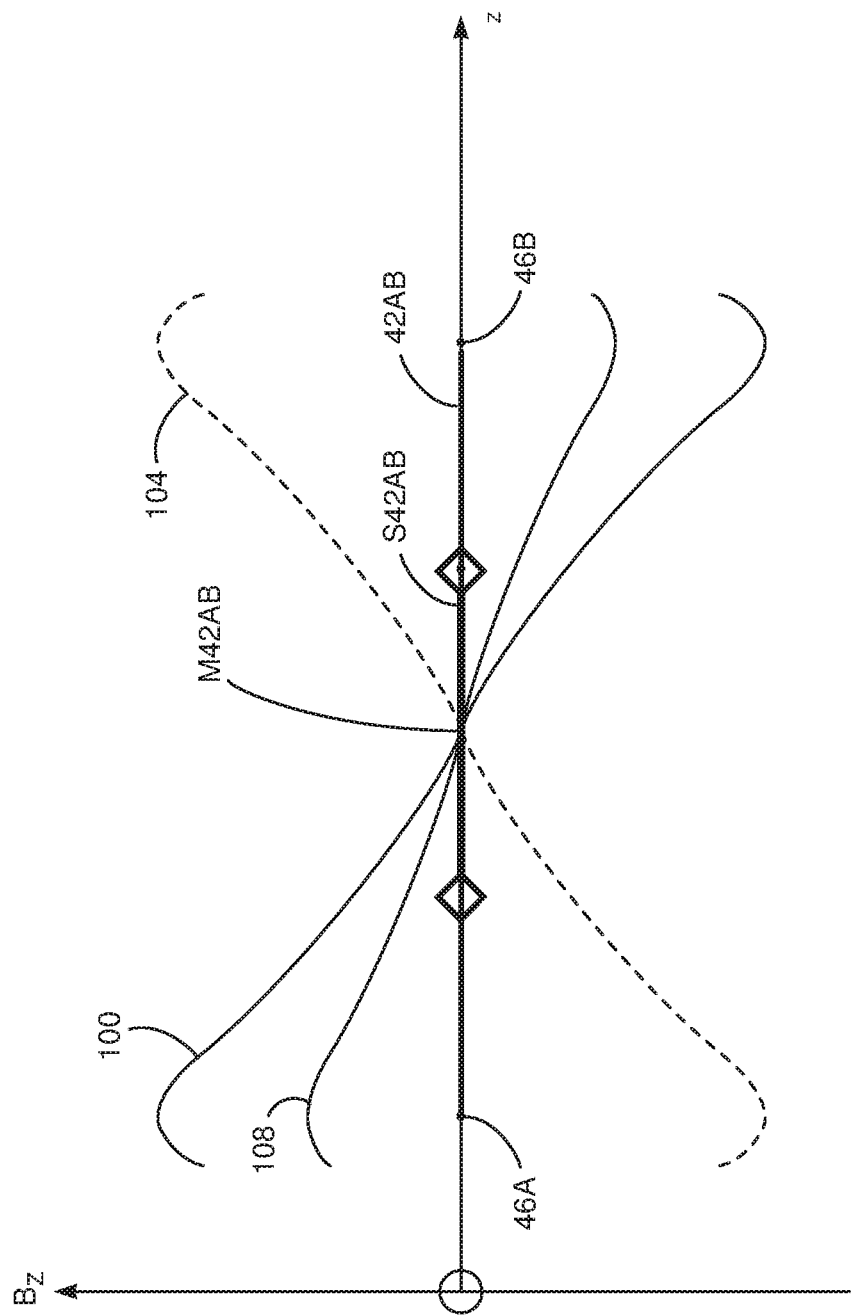
FIG. 4 shows schematic graphs of magnetic field intensity vs. distance for a coil pair, according to an embodiment of the present invention.

FIG. 4 shows schematic graphs of magnetic field intensity vs. distance for coil pair (42A, 42B), according to an embodiment of the present invention. Alternating current power supply 94 is configured to drive each of the coils of the pair sinusoidally, with a frequency, i.e., a temporal rate of change, of, in one embodiment, approximately 10 kHz, and the coils are driven in anti-phase, i.e., at any given instance the currents in the coils are equal in magnitude but opposite in direction. In other embodiments the driving frequency may be different from 10 kHz, for example approximately 20 kHz. The driving frequency for each of the pairs is different. The anti-phase driving may be implemented either by winding the coils in opposite directions, and powering them with in-phase current, or by winding the coils in the same direction, and powering them with out-of-phase current.

As described above, line segment 42AB defines a common symmetry axis for the coils, and by virtue of the symmetry, the magnetic field direction from each coil on the axis of symmetry is along the axis. On the axis the field magnitudes from the two coils add, but because the coils are driven in anti-phase, the resultant field at any given point on the axis varies along the axis. (This is in contrast to coils operated as a Helmholtz pair, where the currents of the pair of coils are in phase, and where the resultant field on the axis is substantially non-variant along a section of the axis between the coils.)

A graph 100 shows the field magnitude $B_z$, in the z-direction along a z-axis including points of line segment 42AB, at a first time when the alternating current to coil 42A is a maximum, so that the alternating current to coil 42B is a minimum. A graph 104 shows $B_z$ at a second time when the alternating current to coil 42A is a minimum, so that the alternating current to coil 42B is a maximum. The two graphs illustrate the extents of the values of $B_z$ as coils 42A, 42B are driven in anti-phase. By way of example, a graph 108 illustrates extents of the values of $B_z$ at an intermediate time between the first and second times referred to above.

It will be understood that the instantaneous magnetic fields on line segment 42AB oscillate in time between values shown by graphs 100 and 104. While the oscillation occurs, the value of $B_z$ at midpoint M42AB is zero. In addition, and as illustrated by the graphs, at any given time instant the variation of $B_z$, along points of the z-axis comprising line segment 42AB, is monotonic.

In addition to being monotonic, some embodiments comprise a sub-section of line segment 42AB, centered on midpoint M42AB, wherein $B_z$ varies linearly with z. By way of example, FIG. 4 shows a sub-section S42AB of line segment 42AB (the segment terminating in diamonds) having such a linear variation. Alternatively, other embodiments comprise no such linear variation sub-section.

Embodiments of the present invention are assumed to have a linear variation sub-section if the separation $d_{42AB}$ between coils 42A and 42B is within a range given by R and 2.8R where R is the radius of coils 42A, 42B. If the separation is outside this range, for example, if the separation is between 0.5R and R, there is no linear sub-section.

The description above of the magnetic field applies to the field on the symmetry axis of the coils, and also applies approximately to positions close to, but not on, the axis, i.e., the z-axis. Because of the monotonic variation of the magnetic field with distance along the axis, there is a one-to-one correspondence between a measured value of the amplitude of the magnetic field and a z-position on, or close to, the z-axis. Thus for any given magnetic field amplitude $B_{g1}$ there is an xy plane at a unique position on the z-axis. Moving further from the z-axis, the xy plane for $B_{g1}$ extends as a three-dimensional (3D) curved surface, in xyz space, which is symmetrical about the z-axis.

Coil pairs which are non-circular have the same general properties as pairs of circular coils. I.e., there is a monotonic variation of the magnetic field with distance along the symmetry axis, herein considered to be the x-axis, and because of the monotonic variation, there is a one-to-one correspondence between a measured value of the magnetic field amplitude and an x-position on, or close to, the x-axis. Similarly, for any given magnetic field amplitude $B_{g2}$ there is a yz plane at a unique position on the x-axis. Moving further from the x-axis, the yz plane for $B_{g2}$ extends as a 3D curved surface, in xyz space, which is symmetrical about the x-axis.

Figure 5:
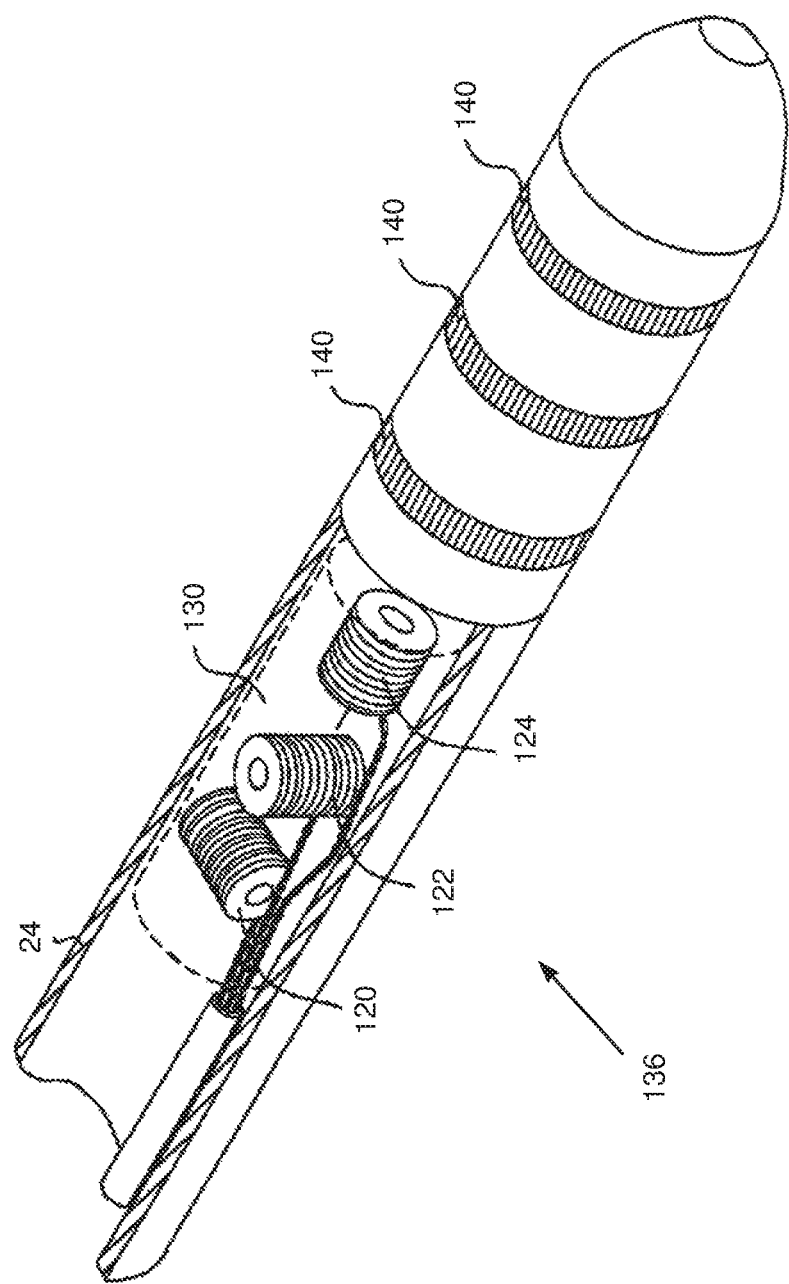
FIG. 5 is a schematic partially cut-away diagram of a probe, according to an embodiment of the present invention.

FIG. 5 is a schematic partially cut-away diagram of probe 24, according to an embodiment of the present invention. Probe 24 comprises three similar conductive coils 120, 122, 124 wound on respective formers, the coils being fixedly disposed within a hollow region 130 of the probe so that symmetry axes of the coils are orthogonal to each other. If an alternating magnetic field traverses the coils, the coils in response generate alternating current signals depending, inter alia, on the amplitude of the magnetic field. Measuring the generated currents thus provides a measure of the traversing magnetic field, so that the three coils act as a sensor of the magnetic field, and are herein also referred to as sensor 136. As stated above, in the description herein probe 24 is assumed to be used for ablation, and the probe comprises electrodes 140 that may be used for transferring RF energy for the ablation. In some embodiments, rather than sensor 136 comprising three separated orthogonal coils, the sensor is configured as three similar conductive orthogonal coils wound on a single former.

Figure 6:
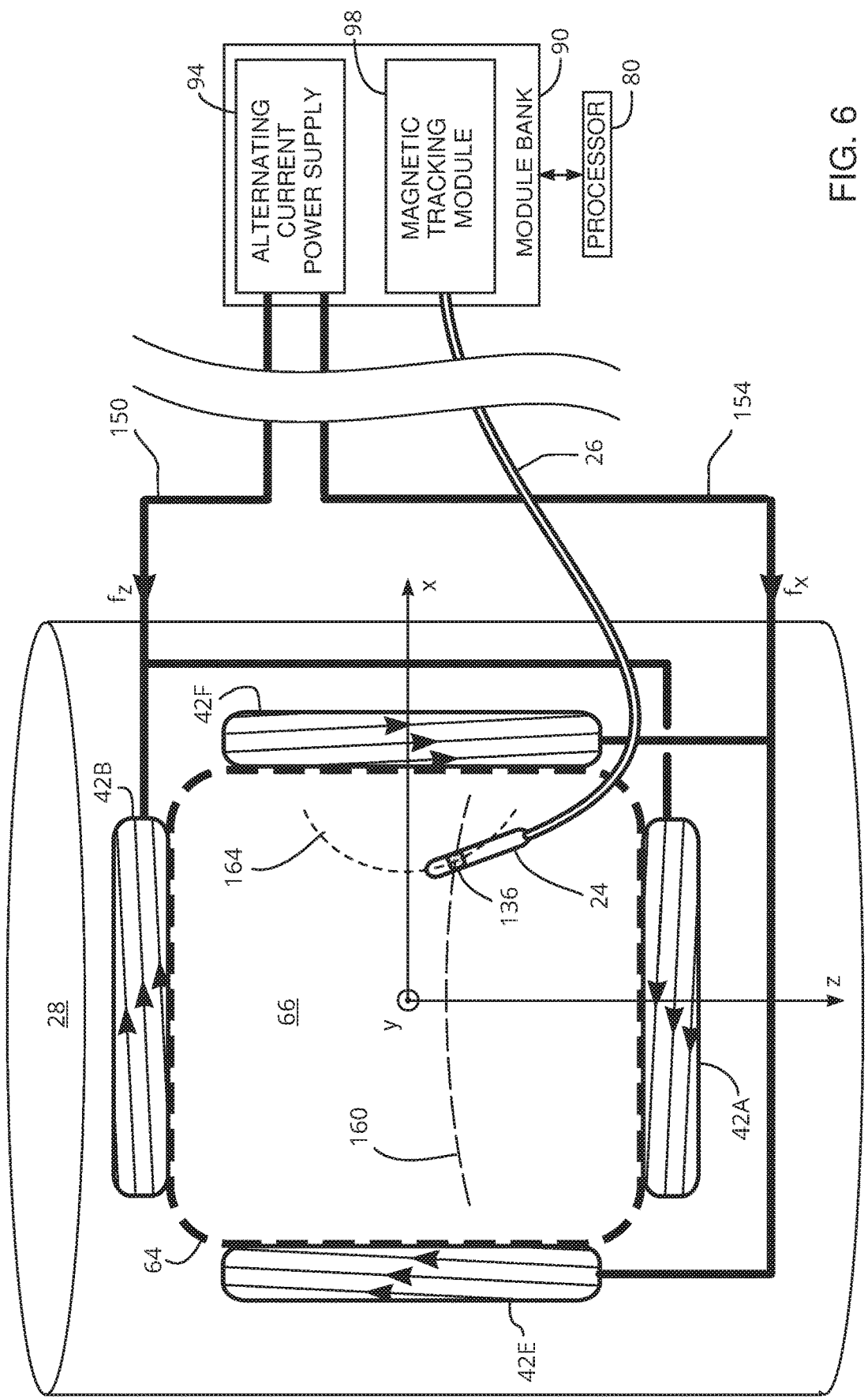
FIG. 6 is a schematic diagram of elements of the apparatus of FIG. 1 in operation, according to an embodiment of the present invention.

FIG. 6 is a schematic diagram of elements of apparatus 20 in operation, according to an embodiment of the present invention. The diagram shows a view from above bore 28, down the y-axis, and illustrates some elements of apparatus 20 within the bore, as well as some external elements. Thus, coil pairs (42A, 42B) on the z-axis, and coil pairs (42E, 42F) on the x-axis, are shown, but for clarity coil pairs (42C, 42D) on the y-axis are not shown. The coils are shown attached to frame 64, and probe 24, comprising sensor 136, has been introduced into volume 66 within the frame. The frame and its attached coils are assumed to have been calibrated, and the calibration is explained below with reference to the flowchart of FIG. 7.

Alternating current power supply 94 is connected to coil pairs (42A, 42B), on the z-axis, by a cable 150, and drives the coils in anti-phase, as indicated by the oppositely directed arrows within the coils, with a frequency $f_z$. The power supply is also connected to coil pairs (42E, 42F), on the x-axis, by a cable 154, and drives these coils in anti-phase with a frequency $f_x$. While not shown in the diagram, coils (42C, 42D) are driven in anti-phase by power supply 94 at a frequency $f_y$. Frequencies $f_x$, $f_y$, and $f_z$ are typically selected so that they are separated sufficiently to be easily filtered, one from another.

As explained above, coils 42 generate three sets of alternating magnetic fields in volume 66, the fields alternating with respective frequencies $f_x$, $f_y$, and $f_z$. The alternating magnetic fields generate respective signals in sensor 136 of probe 24, and the signals are received by magnetic tracking module 98. Processor 80 together with the module analyzes the signals, and for each frequency determines an amplitude of the respective magnetic field generating the respective signal.

Tracking module 98 is assumed to analyze the $f_z$ signals generated in sensor 136, in response to the $f_z$ anti-phase magnetic fields of coils 42A, 42B, and evaluate that the magnetic field amplitude generated by the coils is $B_{g1}$. As explained above, there is a 3D curved surface in volume 66 corresponding to $B_{g1}$, and in the diagram a line 160 corresponds to the curved surface, so that the surface is also referred to herein as surface 160. Similarly, module 98 is assumed to analyze the $f_x$ signals generated in sensor 136, in response to the $f_x$ anti-phase magnetic fields of coils 42E, 42F, and evaluate that the magnetic field amplitude generated by the coils is $B_{g2}$. In the diagram a line 164 illustrates the 3D curved surface, also referred to herein as surface 164, in volume 66 corresponding to $B_{g2}$.

Surfaces 160 and 164 typically intersect in a line, and there is a further surface, not illustrated in the diagram, generated in response to the $f_y$ anti-phase magnetic fields of coils 42C, 42D. The intersection of the three surfaces provides the position of sensor 136, and thus of probe 24, in volume 66.

Figure 7:
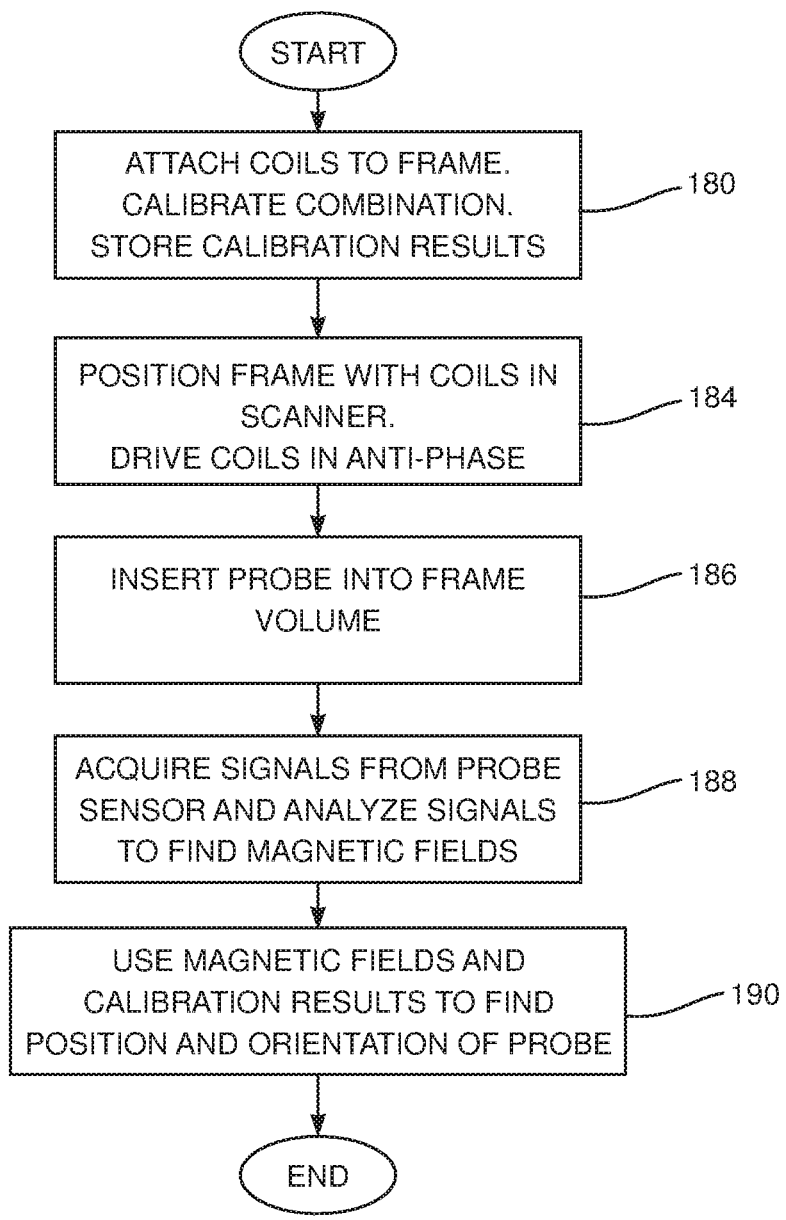
FIG. 7 is a flowchart of steps performed in operation of the apparatus, according to an embodiment of the present invention.

FIG. 7 is a flowchart of steps performed in operation of apparatus 20, according to an embodiment of the present invention. In an initial calibration step 180, coils 42 are attached to frame 64, and the combination of the coils and frame is calibrated. The calibration is typically performed outside scanner 22, although in some cases the calibration may be performed with the frame and coil combination installed in bore 28 of the scanner.

The calibration comprises connecting alternating current power supply 94 to the coils, and operating the power supply, typically using processor 80, to generate the alternating magnetic fields in volume 66. While the magnetic fields are being generated, a calibration magnetic sensor, generally similar to sensor 136, is introduced at known locations within volume 66, Typically the calibration sensor is mounted on an xyz translation stage, and the stage is moved in a step-wise manner. At each position and orientation of the calibration sensor, processor 80 records the magnetic field amplitudes and directions registered by the sensor, for the three different pairs of coils.

Since interpolation of the stored results is typically used in the following operating steps, embodiments having coil pairs generating a linearly varying magnetic field sub-section, described above, may use less calibration positions, since the linearity can be used for the interpolation. While embodiments without a linearly varying magnetic field sub-section may require more calibration positions, such embodiments typically comprise a larger volume 66.

Processor 80 typically stores the sensor positions and orientations, and corresponding magnetic field amplitudes and directions, as a calibration look-up table for use during operation of apparatus 20.

In an operating step 184 patient 34, frame 64 and attached coils 42 are positioned in bore 28 and alternating current power supply 94 is activated to drive the coils in anti-phase, as described above.

In a probe introduction step 186 probe 24 is inserted into volume 66, typically comprising a region of the patient being investigated.

In an analysis step 188 the processor and tracking module acquire signals generated by sensor 136 in response to the magnetic fields traversing the sensor. The processor and the module analyze the acquired signals to determine respective magnetic field amplitudes generated by each of the pairs of coils 42, so generating a magnetic field amplitude $B_1$ from coil pair (42A, 42B), a magnetic field amplitude $B_2$ from coil pair (42C, 42D), and a magnetic field amplitude $B_3$ from coil pair (42E, 42F). As described above with reference to FIG. 6, $B_1$ corresponds to a 3D surface symmetrical about the z-axis, the symmetry axis of pair (42A, 42B), $B_2$ corresponds to a 3D surface symmetrical about the y-axis, the symmetry axis of pair (42C, 42D), and $B_3$ corresponds to a 3D surface symmetrical about the x-axis, the symmetry axis of pair (42E, 42F).

In a final step 190 processor 80 is able to use the calibration look-up table stored in calibration step 180, typically if necessary using interpolation, to evaluate xyz values of the three 3D surfaces, and to find the xyz value of the intersection of the surfaces, so finding the position of probe 24 in volume 66. The processor is also able to use the stored look-up table to find the orientation of probe 24.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
a frame encompassing a volume;
three pairs of separated planar conductive coils, the separated coils of each pair having a common axis of symmetry, the three pairs being attached to the frame so that the common axes of symmetry are mutually orthogonal, and so that the coils surround the volume;
an alternating current power supply coupled to drive the separated coils of each pair sinusoidally in anti-phase so as to generate a magnetic field having a preset spatial variance over the volume;
a probe configured to enter the volume and having a sensor coupled to generate a signal responsive to a temporal rate of change of the magnetic field and to the preset spatial variance thereof; and
a processor, configured to receive the signal, and in response to formulate a position of the probe within the volume.

2. The apparatus according to claim 1, wherein the separated coils of each pair have a common size and shape.

3. The apparatus according to claim 2, wherein the common shape of at least one of the pairs is circular.

4. The apparatus according to claim 2, wherein the common shape of at least one of the pairs is polygonal.

5. The apparatus according to claim 1, wherein the frame and attached pairs have an overall size permitting insertion of the frame and attached pairs into a bore of a magnetic resonance imaging scanner.

6. The apparatus according to claim 1, wherein at least one of the pairs of coils is wound in opposite directions, and the alternating current power supply provides power to the coils in the one of the pairs with in-phase current.

7. The apparatus according to claim 1, wherein at least one of the pairs of coils is wound in a common direction, and the alternating current power supply provides power to the coils in the one of the pairs with out-of-phase current.

8. The apparatus according to claim 1, wherein for a given pair of coils the preset spatial variance of the magnetic field comprises a region wherein the magnetic field is linearly varying along the common axis of symmetry of the given pair.

9. The apparatus according to claim 8, wherein each of the coils of the given pair has a radius R, and wherein a separation between the coils of the given pair is within a range between R and 2.8R.

10. The apparatus according to claim 1, wherein for a given pair of coils the preset spatial variance of the magnetic field comprises no region wherein the magnetic field is linearly varying along the common axis of symmetry of the given pair.

11. The apparatus according to claim 10, wherein each of the coils of the given pair has a radius R, and wherein a separation between the coils of the given pair is outside a range between R and 2.8R.

12. The apparatus according to claim 1, wherein the alternating current power supply is coupled to drive each of the three pairs of coils sinusoidally in anti-phase at different respective frequencies, so as to generate the temporal rate of change of the magnetic field.

13. The apparatus according to claim 1, wherein the three pairs of coils comprise three respective midpoints, and wherein the three pairs are attached to the frame so that the three midpoints are located at a single point.

14. The apparatus according to claim 1, wherein the processor is configured to formulate an orientation of the probe within the volume in response to the received signal.

15. A method, comprising:
encompassing a volume with a frame;
attaching to the frame three pairs of separated planar conductive coils, the separated coils of each pair having a common axis of symmetry, so that the common axes of symmetry are mutually orthogonal, and so that the coils surround the volume;
coupling an alternating current power supply to drive the separated coils of each pair sinusoidally in anti-phase so as to generate a magnetic field having a preset spatial variance over the volume;
inserting a probe into the volume, the probe having a sensor coupled to generate a signal responsive to a temporal rate of change of the magnetic field and to the preset spatial variance thereof; and
receiving the signal, and in response formulating a position of the probe within the volume.

16. The method according to claim 15, wherein the separated coils of each pair have a common size and shape.

17. The method according to claim 16, wherein the common shape of at least one of the pairs is circular.

18. The method according to claim 16, wherein the common shape of at least one of the pairs is polygonal.

19. The method according to claim 15, wherein the frame and attached pairs have an overall size permitting insertion of the frame and attached pairs into a bore of a magnetic resonance imaging scanner.

20. The method according to claim 15, wherein at least one of the pairs of coils is wound in opposite directions, and the alternating current power supply provides power to the coils in the one of the pairs with in-phase current.

21. The method according to claim 15, wherein at least one of the pairs of coils is wound in a common direction, and the alternating current power supply provides power to the coils in the one of the pairs with out-of-phase current.

22. The method according to claim 15, wherein for a given pair of coils the preset spatial variance of the magnetic field comprises a region wherein the magnetic field is linearly varying along the common axis of symmetry of the given pair.

23. The method according to claim 22, wherein each of the coils of the given pair has a radius R, and wherein a separation between the coils of the given pair is within a range between R and 2.8R.

24. The method according to claim 15, wherein for a given pair of coils the preset spatial variance of the magnetic field comprises no region wherein the magnetic field is linearly varying along the common axis of symmetry of the given pair.

25. The method according to claim 24, wherein each of the coils of the given pair has a radius R, and wherein a separation between the coils of the given pair is outside a range between R and 2.8R.

26. The method according to claim 15, wherein the alternating current power supply is coupled to drive each of the three pairs of coils sinusoidally in anti-phase at different respective frequencies, so as to generate the temporal rate of change of the magnetic field.

27. The method according to claim 15, wherein the three pairs of coils comprise three respective midpoints, and wherein the three pairs are attached to the frame so that the three midpoints are located at a single point.

28. The method according to claim 15, and comprising formulating an orientation of the probe within the volume, in response to the received signal.

* * * * *